(12) United States Patent
Claiborne et al.

(10) Patent No.: US 6,207,687 B1
(45) Date of Patent: Mar. 27, 2001

(54) SUBSTITUTED IMIDAZOLES HAVING CYTOKINE INHIBITORY ACTIVITY

(75) Inventors: Christopher F. Claiborne, Lansdale; Nigel J. Liverton, Harleysville; David A. Claremon, Maple Glen, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/358,199

(22) Filed: Jul. 21, 1999

Related U.S. Application Data
(60) Provisional application No. 60/095,051, filed on Jul. 31, 1998.

(51) Int. Cl.[7] ..................... A61K 31/4439; C07D 401/04
(52) U.S. Cl. ......................................... 514/341; 546/274.1
(58) Field of Search ........................... 546/274.1; 514/341

(56) References Cited

U.S. PATENT DOCUMENTS

| | | |
|---|---|---|
| 5,670,527 | 9/1997 | Adams et al. . |
| 5,783,664 | 7/1998 | Lee et al. . |
| 5,965,583 | 10/1999 | Beers et al. . |

FOREIGN PATENT DOCUMENTS

| | | |
|---|---|---|
| WO 99/32121 | 7/1999 | (WO) . |

OTHER PUBLICATIONS

J. Chin and M.J. Kostura, *J. Immunol.*, 151:5574–5585 (1993).
G. Poli, et al., *Proc. Natl. Acad. Sci.* USA, 87:782–785 (1990).
C.A. Dinarello, *Rev. Infect. Disease*, 6:51 (1984).
K. Hagiwara, et al., *Database CAPLUS on STN*, No. 127:34213 (1997).

*Primary Examiner*—Patricia L. Morris
(74) *Attorney, Agent, or Firm*—Shu Muk Lee; David L. Rose; Mark R. Daniel

(57) ABSTRACT

There are disclosed compounds of formula (I)

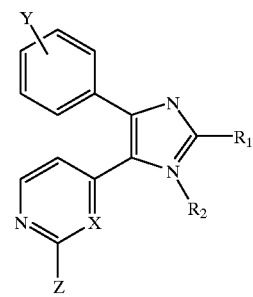

and pharmaceutically acceptable salts thereof which may be useful for the treatment of cytokine mediated diseases such as arthritis.

4 Claims, No Drawings

SUBSTITUTED IMIDAZOLES HAVING CYTOKINE INHIBITORY ACTIVITY

This application claims the benefit of U.S. patent application Ser. No. 60/095,051, filed Jul. 31, 1998.

BACKGROUND OF THE INVENTION

The present invention relates to substituted imidazole compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells which are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention relates to a compound represented by formula I:

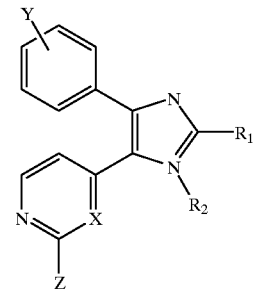

wherein $R_1$ is $C_{1-6}$ alkyl;

$R_2$ is H, $C_{1-6}$ alkyl, $C_{3-8}$ cycloalkyl, $OC_{1-6}$ alkyl or $C(O)C_{1-6}$ alkyl;

$R_3$ is H, $C_{1-6}$ alkyl, $C_{3-8}$ cycloalkyl, $OC_{1-6}$ alkyl or $C(O)C_{1-6}$ alkyl, or aralkyl;

X is C or N;

Y is H, halogen, $C_{1-6}$ alkyl, CN or $CF_3$;

Z is $NHR_3$ or F;

or a pharmaceutically acceptable addition salt and/or hydrate thereof, or where applicable, a geometric or optical isomer or racemic mixture thereof.

A pharmaceutical composition is also included in the invention described herein, which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective to treat said cytokine mediated disease.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

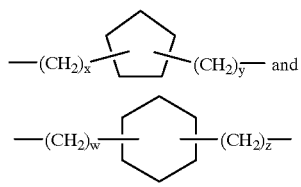

wherein:

x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon—carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups.

Substituted alkyl and aryl, and the substituted portions of aralkyl, aralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, and sulfonylamino.

Aralkyl refers to the group —$C_{1-6}$ alkylaryl.

Halo means Cl, F, Br and I selected on an independent basis.

As used herein, the term "composition" is intended to encompass a product comprising the specified ingredients in the specified amounts, as well as any product which results, directly or indirectly, from combination of the specified ingredients in the specified amounts.

The term "TNF mediated disease or disease state" refers to disease states in which TNF plays a role, either by production or increased activity levels of TNF itself, or by causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor-beta (TNF-b).

By the term "cytokine interfering or cytokine suppresive amount" is mean an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the present invention may contain one or more asymmetric carbon atoms and may exist in racemic and optically active forms. All are within the scope of the present invention.

One subset of compounds of the present invention which is of interest relates to compounds of formula I wherein $R_2$ is $C_{3-8}$ cycloalkyl with cyclopentyl a particularly preferred cycloalkyl group.

Representative examples of compounds of the present invention include the following species:

1-(S)-phenyl-N-{4-[3-cyclopentyl-2-methyl-5-(3-trifluoromethyl-phenyl)-3H-imidazol-4-yl]-pyridin-2-yl}-ethylamine; as well as pharmaceutically acceptable salts thereof.

The compounds of the present invention are prepared generally by procedures illustrated in the accompanying scheme.

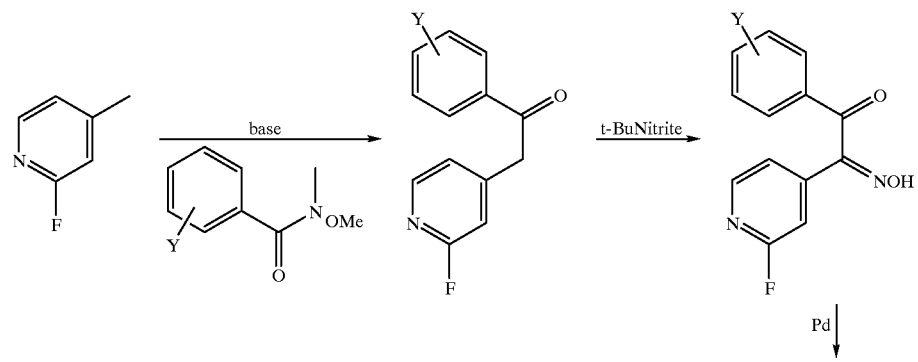

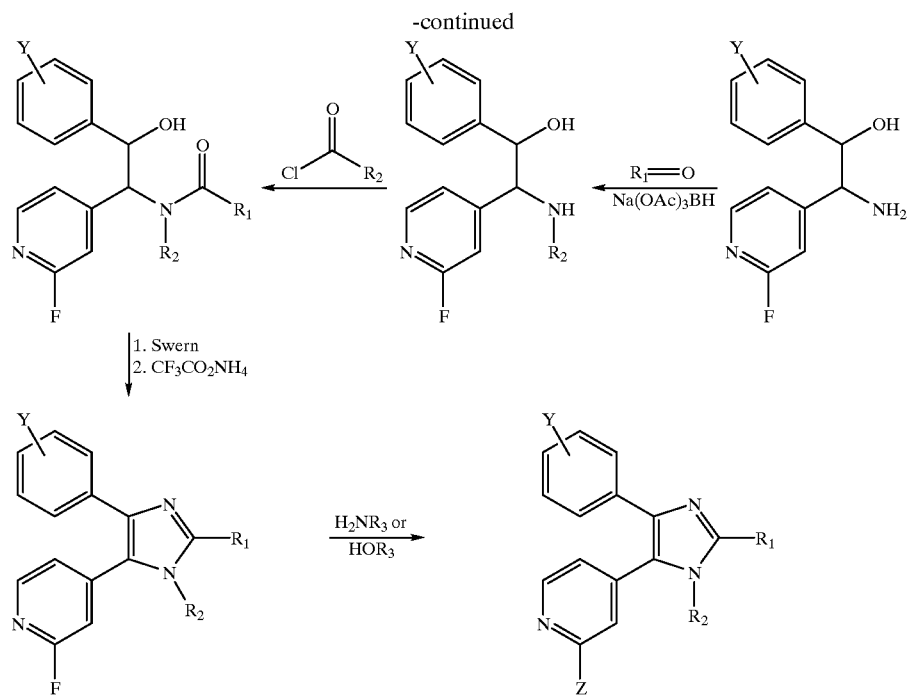
In particular, a Preferred compound of the invention is prepared as illustrated below in scheme 1.
Reaction Scheme 1
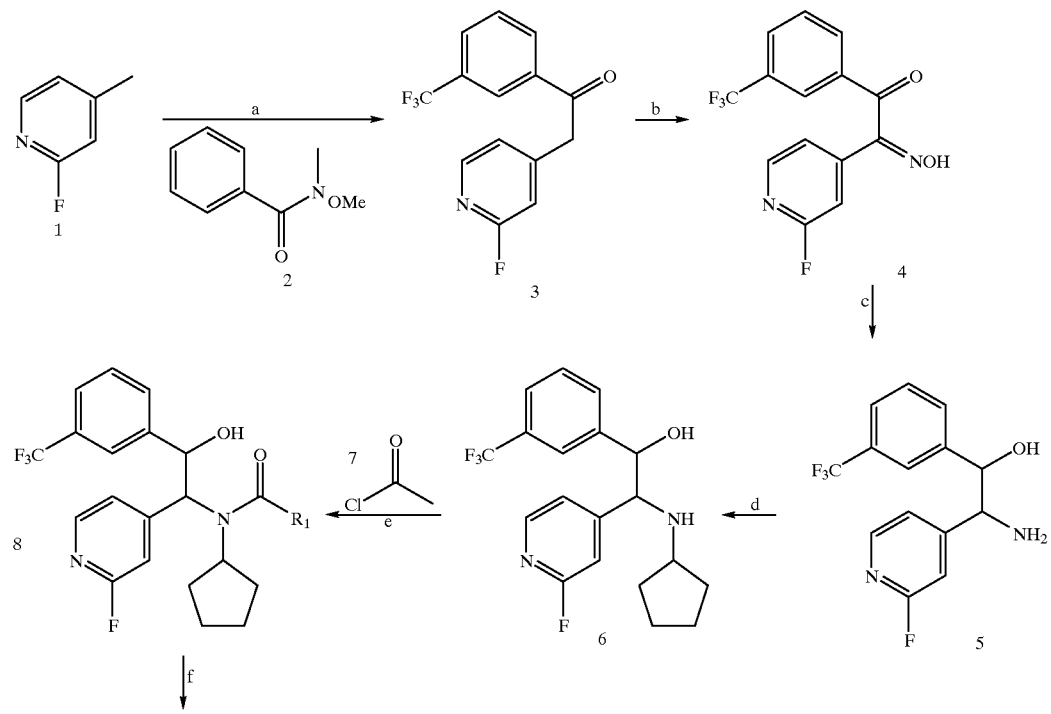

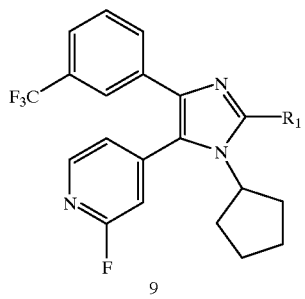
-continued
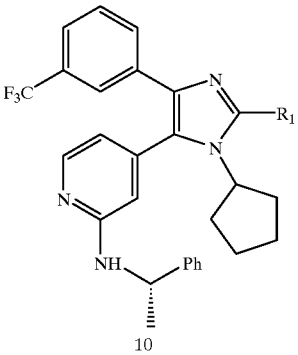

Reagents and Conditions:
a) n-BuLi (1.05 equiv.), 1, THF at −78° C., then 2 (80%);
b) t-BuNitrite, HCl, 3, ethanol at −5° C. for 1 hr, then 2 hrs at 23° C. (95%);
c) 10% Pd/C (30% by wt. of substate), 4, H2 (1 atm) in ethanol for 12 hrs (91%);
d) 5, Na(OAc)3BH (2.0 equiv.), cyclopentanone (1.5 equiv.) in 1,2 dichloroethane at 25° C. for 15 hrs. (92%);
e) 6 (1.0 equiv.), DIPEA (2.0 equiv.) in methylene chloride at −10° C., 7 (1.1 equiv.), 2 hrs. (95%);
f) DMSO (3 equiv.) and oxalyl chloride (2.5 equiv.) in methylene chloride at −78° C., then 8. After 2 hrs triethylamine (5.0 equiv.) and warm to 23° C.; Unpurified ketone from 8 in ammonium trifluoroacetate (as solvent) at 150° C. for 5 min. (53%);
g) 9 in (S)-(−)-α-methylbenzylamine (10 equiv.) at 150° C. for 15 hrs (76%).

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula I include conventional non-toxic salts or quarternary ammonium salts of the compounds of formula I formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound as described herein in combination with a pharmaceutically acceptable carrier.

The invention described herein also includes a method of treating a cytokine mediated disease in a mammal, comprising administering to a mammalian patient in need of such treatment an amount of a compound as described herein in an amount which is effective to treat said cytokine mediated disease.

Of particular interest is a method of treating inflammation in a mammalian patient in need of such treatment, which is comprised of administering to said patient an anti-inflammatory effective amount of a compound as described herein.

Another method which is of particular interest is a method of treating a cytokine mediated disease as described herein wherein the disease is osteoporosis.

Another method which is of particular interest is a method of treating a cytokine mediated disease as described herein wherein the disease is rheumatoid arthritis or osteoarthritis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of inhibiting a cytokine or cytokines in a mammal in need thereof, which comprises administering to said mammal an effective amount of a compound of formula I to inhibit said cytokine or cytokines, down to normal levels, or in some cases to subnormal levels, so as to ameliorate, prevent or treat the disease state.

The compounds of formula 1 can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxy-ethylene derivatives thereof. Suspending agents such as natural gums, cellulose derivatives or inorganic materials such as silicas, and other ingredients such as lanolin may also be included.

EXAMPLE 1

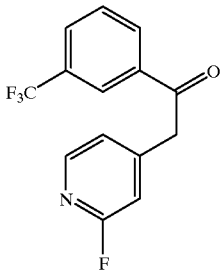

Step A

Preparation of N-methyl-N-methoxy-(3-trifluoro-methyl)phenyl-carboxamide (2) and preparation of 2-(2-Fluoropyridin-4-yl)-1-(3-trifluoromethylphenyl)-ethanone (3)

To a suspension of the N,O-dimethylhydroxylamine hydrochloride (58.2 g, 0.60 mol) in dichloromethane (1 L) at 0° C., under argon, was added 3-trifluoromethylbenzoyl chloride (104.0 g, 0.50 mol) followed by a slow addition (<+5° C.) of triethylamine (152.3 mL, 1.09 mol). The reaction was aged for 30 min. at +5° C. and then allowed to warm to room temperature. TLC (1:1, ethyl acetate/hexane) showed the reaction to be complete. The reaction was then washed with 5% aqueous citric acid (500 mL) and 5% aqueous sodium bicarbonate. The aqueous extracts were back extracted with methylene chloride (100 mL) and the combined methylene chloride extracts were dried over sodium sulfate, filtered and concentrated to an oil. The oil was redissolved in toluene (2×100 mL) and evaporated in vacuo to afford the Weinreb amide (114.7 g, 98%). $^1$H NMR (300 MHz, CDCl$_3$) d 7.98 (s, 1 H, Ar), 7.89 (d, J=7.8 Hz, 1 H, Ar), 7.72 (d, J=7.8 Hz, 1 H, Ar), 7.55 (t, J=7.8 Hz, 1 H, Ar), 3.55 (s, 3 H, CH$_3$O), 3.39 (s, 3 H, CH$_3$N).

To a stirring solution of diisopropylamine (17.69 mL, 0.135 mol) in anhydrous THF (200 mL) at −78° C., under argon, was added n-butyllithium (54.0 mL, 2.5M in hexane, 0.135 mol), followed after 5 min. by a solution of 2-fluoro-4-methylpyridine (10 g, 0.090 mol) in anhydrous THF (20 mL). After stirring for 15 min. at −78° C., a solution of N-methoxy-N-methyl-3-trifluoromethylbenzamide (2) (23.08 g, 0.099 mol) in anhydrous THF (10 mL) was added to the reaction mixture which was then stirred for 5 min., and allowed to warm to 0° C. The reaction was quenched with water (400 mL), and extracted with ethyl acetate (3×200 mL). The ethyl acetate extracts were combined, dried over anhydrous sodium sulfate, filtered, and concentrated to an oil which was chromatographed on silica gel (1 kg), eluting with 20% ethyl acetate in hexane to give 21.6 g (85%) of the title compound. $^1$H NMR (300 MHz, CDCl$_3$) d 8.25 (s, 1 H, Pyr), 8.20 (d, J=5.1 Hz, 1 H, Pyr), 8.18 (d, J=9.3 Hz, 1 H, Pyr), 7.88 (d, J=7.8 Hz, Ar), 7.67 (t, J=7.8 Hz, 1 H, Ar), 7.09 (d, J=5.1 Hz, 1 H, Ar), 6.86 (s, 1 H, Ar), 4.37 (s, 2 H, PyrCH$_2$C).

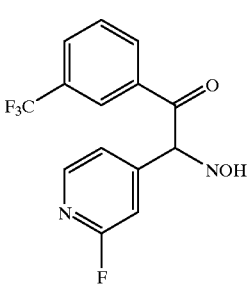

Step B

Preparation of 1-(2-Fluoropyridin-4-yl)-2-(3-trifluoromethylphenyl)-ethane-1,2-dione 1-oxime (4)

To a mixture of 2-(2-fluoropyridin-4-yl)-1-(3-trifluoromethyl-phenyl)ethanone (3) (10.80 g, 0.038 mol) in ethanol (200 mL), at −10° C., under argon, was added tert-butyl nitrite (5.0 mL, 0.042 mol) and hydrochloric acid (12.2 mL, 2.5M in ethanol, 0.031 mol) dropwise while maintaining the temperature below −5° C. Upon completion of additions, the reaction was allowed to warm to RT for 2 hrs. The reaction mixture was then concentrated in vacuo, diluted with water (100 mL), basified with saturated sodium bicarbonate (200 ml), and extracted with ethyl acetate (3×400 mL). The combined organic layers were washed with water (300 mL), dried with brine (300 mL) and anhydrous sodium sulfate, filtered and concentrated to an oil which weighed 11.4 g (95%). $^1$H NMR (300 MHz, CDCl$_3$) d 8.31 (s, 1 H, Ar), 8.29 (d, J=5.3 Hz, 1 H, Pyr), 8.24 (d, J=7.8 Hz, 1 H, Ar), 7.92 (d, J=8.1 Hz, 1 H, Ar), 7.71 (t, J=7.8 Hz, 1 H, Ar), 7.40 (d, J=5.1 Hz, 1 H, Pyr), 7.23 (s, 1 H, Pyr).

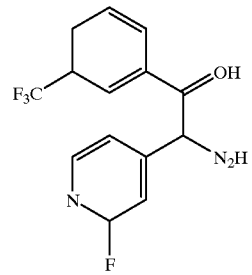

Step C

Preparation of 2-amino-2-(2-fluoro-pyridin-4-yl)-1-(3-trifluoromethyl-phenyl)-ethanol (5)

10% palladium on carbon (3.0 g) was added to a solution of the 1-(2-fluoropyridin-4-yl)-2-(3-trifluoromethylphenyl)-ethane-1,2-dione 1-oxime (4) (8.0 g, 27 mmol) in ethanol (400 mL) at ambient temperature. The reaction vessel was vacuum purged with hydrogen and vigorously stirred for 10 hrs. After the reaction was complete, the solution was filtered through a pad of celite, and concentrated to give a yellow solid. The residue could be purified by recrystalization from methylene chloride and hexane. Alternatively, non polar impurities could be removed by filtration though silica gel starting with 5% methanol in methylene chloride to 5% methanol, 0.5% ammonium hydroxide in methylene chloride. Colorless solid (91%): mp 128–129° C.; $^1$H NMR (300 MHz, CD$_3$OD) d 8.01 (d, J=5.0 Hz, 1 H, Ar), 7.53 (m, 1 H, Ar), 7.49 (m, 2 H, Ar), 7.43 (s, 1 H, Ar), 7.06 (d, J=5.0 Hz, 1 H, Ar), 6.86 (s, 1 H, Ar), 4.96 (d, J=5.0 Hz, 1 H, CH), 4.12 (d, J=5.0 Hz, 1 H, CH).

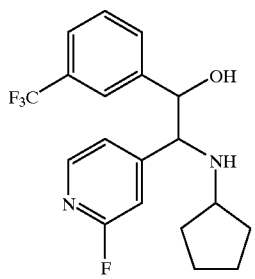

Step D
Preparation of 2-(2-fluoro-pyridin-4-yl)-2-cyclopentylamino-1-(3-trifluoromethyl-phenyl)-ethanol (6)

The 2-amino-2-(2-fluoro-pyridin-4-yl)-1-(3-trifluoromethyl-phenyl)-ethanol (5) (1.0 g, 3.3 mmol), cyclopentanone (0.42 g, 5.0 mmol), and Na(OAc)$_3$BH (1.4 g, 6.7 mmol) in 1,2 dichloroethane (20 mL) were stirred under argon at RT for 15 hrs. The resulting mixture was treated with sat. aqueous NaHCO$_3$ (50 mL), extracted with ethyl acetate (3×75 mL), dried (sodium sulfate), and concentrated. The resulting residue was purified by silica gel chromatography using 50% ethyl acetate in methylene chloride to give the title product (1.1 g, 92%). $^1$H NMR (300 MHz, CDCl$_3$) d 8.05 (d, J=4.9 Hz, 1 H, Pyr), 7.51 (d, J=7.9 Hz, 1 H, Ar), 7.36 (t, J=7.8 Hz, 1 H, Ar), 7.32 (s, 1 H, Ar), 7.22 (d, J=7.9 Hz, 1 H, Ar), 6.81 (d, J=4.9 Hz, 1 H, Pyr), 6.64 (s, 1 H, Pyr), 5.00 (d, J=4.6 Hz, 1 H, PhCHOH), 4.01 (d, J=4.9 Hz, 1 H, CHCHNH), 2.99 (quin, J=3.0 Hz, 1 H, CH$_2$CHCH$_2$), 1.85–1.25 (m, 8 H, CH$_2$).

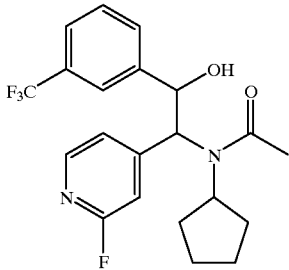

Step E
Preparation of 2-(2-fluoro-pyridin-4-yl)-2-(N-acetyl-cyclopentylamino)-1-(3-trifluoromethyl-phenyl)-ethanol (8):

A stirred solution of 2-(2-fluoro-pyridin-4-yl)-2-cyclopentylamino-1-(3-trifluoromethyl-phenyl)-ethanol (6) (1.0 g, 2.7 mmol) and diisopropylamine (0.95 mL, 5.4 mmol) in methylene chloride (10 mL) was placed under argon and cooled to −10° C. Acetyl chloride (0.21 mL, 3.0 mmol) in methylene chloride (1.0 mL) was slowly added to the reaction mixture. After 2 hrs, ethyl acetate was added (200 mL) followed by aqueous citric acid (50 mL of a 10% solution). The organic layer was then washed with aqueous sodium bicarbonate (50 mL of a sat. solution) and water (50 mL), dried (sodium sulfate), filtered, and concentrated. The crude residue was passed though a pad a silica gel (50% ethyl acetate in hexane) to remove minor impurities, and taken to the next step. Colorless oil (95%): $^1$H NMR (300 MHz, CDCl$_3$) d 8.54 (d, J=5.1 Hz, 1 H, Pyr), 7.49 (m, 4 H, Ar), 6.81 (d, J=5.0 Hz, 1 H, Pyr), 6.72 (s, 1 H, Pyr), 5.63 (s, 1 H, OH), 5.46 (s, 1 H, PhCHOH), 4.34 (s, 1 H, CHCHN), 4.16 (m, 1 H, CH$_2$CHCH$_2$), 2.32 (s, 3 H, COCH$_3$), 1.90 (m, 1 H, CH$_2$), 1.60 (m, 7 H, CH$_2$).

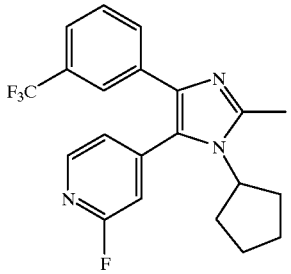

Step F
Preparation of 1-cyclopentyl-5-(2-fluoro-pyridin-4-yl)-2-methyl-4-(3-trifluoromethyl-phenyl)-1H-imidazole (9)

Oxalyl chloride (0.53 mL, 6.1 mmol) was added to a solution of dimethyl sulfoxide (0.52 mL, 7.3 mmol) in methylene chloride (10 mL) at −78 ° C. After 20 min., 2-(2-fluoro-pyridin-4-yl)-2-(N-acetyl-cyclopentyl-amino)-1-(3-trifluoromethyl-phenyl)-ethanol (8) (1.0 g, 2.4 mmol) in methylene chloride (1.0 mL) was added and the reaction solution was stirred at −78° C. for 2 hrs. Triethylamine (1.7 mL, 12.2 mmol) was added and the cooling bath was removed. The solution was diluted with ethyl acetate (150 mL), washed with aqueous ammonium chloride (75 mL) and brine (75 mL), dried (sodium sulfate), and concentrated to give the ketone. This ketone was then transferred to a flask containing anhydrous ammonium trifluoroacetate (4 g) using a minimum amount of ether-methylene chloride. The mixture was placed under vacuum to remove the solvent, and then placed in a preheated oil bath (150° C.). Once all solid had melted and efficient stirring was achieved (approx. 10 min.) the formation of the imidazole was found to be complete. The heating bath was removed and the solids were partitioned between ethyl acetate and water (150/50 mL). The organic layer was dried (sodium sulfate), filtered, and concentrated. The product was purified by silica gel chromatography using 75% ethyl acetate in methylene chloride. Colorless solid (53%): $^1$H NMR (300 MHz, CDCl$_3$) d 8.32 (d, J=5.2 Hz, 1 H, Pyr), 7.71 (s, 1 H, Ar), 7.42 (d, J=7.3 Hz, 1 H, Ar), 7.36 (d, J=7.9 Hz, 1 H, Ar), 7.29 (t, J=7.6 Hz, 1 H, Ar), 7.13 (d, J=5.2 Hz, 1 H, Pyr), 6.88 (s, 1 H, Pyr), 4.30 (quin, J=9.0 Hz, 1 H, CH), 2.62 (s, 3 H, CH$_3$), 2.09–1.62 (m, 8H, CH$_2$).

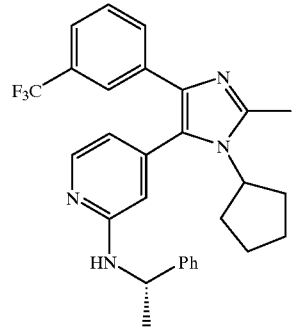

Step G
Preparation of 1-(S)-phenyl-N-{4-[3-cyclopentyl-2-methyl-5-(3-trifluoromethyl-phenyl)-3H-imidazol-4-yl]-pyridin-2-yl}-ethylamine (10) (L-845,722)

A stirred solution of 1-cyclopentyl-5-(2-fluoro-pyridin-4-yl)-2-methyl-4-(3-trifluoromethyl-phenyl)-1H-imidazole (9) (0.25 g, 0.64 mmol) in S-(−)-a-methylbenzylamine (0.78 g, 6.4 mmol) was heated at 150° C. for 15 hrs. The heating bath was removed and the contents of the flask were partitioned between ethyl acetate (100 mL) and pH 4.5 buffer (50 mL composed of 10% citric acid that was treated with 10 N sodium hydroxide to achieve a pH of 4.5). The organic layer was dried (sodium sulfate), filtered, and concentrated. The residue was purified by silica gel chromatography to yield the desired product (73%). White foam: $^1$H NMR (300 MHz, CDCl$_3$) d 8.16 (d, J=5.2 Hz, 1 H, Pyr), 7.76 (s, 1 H, Ar), 7.38–7.19 (m, 8 H, Ar), 6.49 (d, J=5.2 Hz, 1 H, Pyr), 5.17 (d, J=5.8 Hz, 1 H, NH), 4.61 (quin, J=6.4 Hz, 1 H, CH$_2$CHN), 4.07 (q, J=8.6 Hz, 1 H, PhCHCH$_3$), 2.53 (s, 3 H, NCCH$_3$), 1.54 (d, J=6.7 Hz, 3 H, PhCHCH$_3$), 1.82–1.44 (m, 8H, CH$_2$).

BIOLOGICAL ASSAYS
Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (1.0 mL) of the cells is quickly dispensed into each well of a 96 well plate containing 1.0 mL of the test compound, at the appropriate dilution, and are incubated for 24 hours, at 37° C. in 5% CO$_2$. At the end of the culture period, cell culture supernatants are assayed for IL-1b, TNF-a, IL-6 and PGE$_2$ production using specific ELISA.

IL-1 Mediated Cytokine Production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 U/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution, and are incubated for 24 hours, at 37° C. in 5% CO$_2$. At the end of the culture period, cell culture supernatants are assayed for TNF-a, IL-6 and PGE$_2$ synthesis using specific ELISA.

Determination of IL-1b, TNF-a, IL-6 and Prostanoid Production from LPS or IL-1 Stimulated PBMC's IL-1b ELISA Human IL-1b can be detected in cell-culture supernatants or whole blood with the following specific trapping ELISA. Ninety-six well plastic plates (Immunol 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Md.) diluted in Dulbecco's phosphate-buffered saline (—MgCl$_2$, —CaCl$_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1b standards are prepared from purified recombinant IL-1b produced from *E. coli*. The highest concentration begins at 10 ng/mL followed by 11 two-fold serial dilutions. For detection of IL-1b from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1b polyclonal antisera diluted 1:500 in PBS-Tween is added to the plate and incubated for 1 hour at room temperature followed by six washes with PBS-Tween. Detection of bound rabbit anti-IL-1b IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-a ELISA

Immulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-a polyclonal serum purchased from Genzyme. All other operations are identical to those described above for IL-1b. The standards are prepared in PBS-Tween +10% FBS or HS. Eleven 2 fold dilutions are made beginning at 20 ng/mL TNF-a.

IL-6 ELISA

Levels of secreted human IL-6 are also determined by specific trapping ELISA as described previously in Chin and Kostura, *J. Immunol.* 151, 5574–5585 (1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1b. The standards are prepared in PBS-Tween +10% FBS or HS. Eleven 2 fold dilutions are made beginning at 50 ng/mL IL-6.

PGE$_2$ Production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 µl) into gelatin coated 96-well plates. Prior to use, culture medium is replaced with fresh medium (200 µl). Buffer or test compound (25 µl, at appropriate concentrations) is then added to each well in quadruplicate wells and the plates incubated for 6 h in a humidified incubator at 37° C. in an atmosphere of 5% CO$_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. IC50 values where appropriate are generated by non-linear regression analysis.

What is claimed is:

1. A compound represented by formula I:

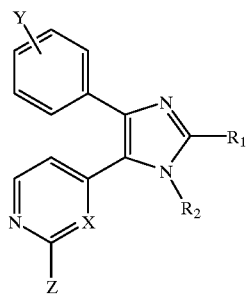

(I)

wherein $R_1$ is $C_{1-6}$alkyl;

$R_2$ is H, $C_{1-6}$alkyl, $C_{3-8}$cycloalkyl, $OC_{1-6}$alkyl or $C(O)C_{1-6}$alkyl;

$R_3$ is H, $C_{1-6}$alkyl, $C_{3-8}$cycloalkyl, $OC_{1-6}$alkyl, $C(O)C_{1-6}$alkyl or $(C_{1-6}$alkyl$)C_{6-10}$aryl;

X is C;

Y is H, halogen, $C_{1-6}$alkyl, CN or $CF_3$;

Z is $NHR_3$ or F;

or a pharmaceutically acceptable addition salt and/or hydrate thereof, or geometric or optical isomer or racemic mixture thereof.

2. A compound as defined in claim 1 wherein $R_2$ is $C_{3-8}$ cycloalkyl.

3. A compound represented by the formula

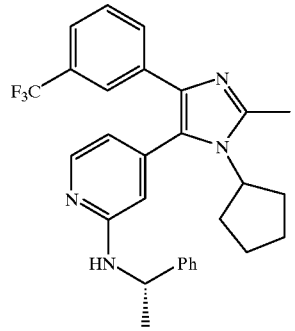

or a pharmaceutically acceptable addition salt and/or hydrate thereof, or where applicable, a geometric or optical isomer or racemic mixture thereof.

4. A pharmaceutical composition which is comprised of an effective amount of a compound in accordance with claim 1 in combination with a pharmaceutically acceptable carrier.

* * * * *